United States Patent
Chordia et al.

(10) Patent No.: US 8,246,834 B2
(45) Date of Patent: Aug. 21, 2012

(54) HIGH PRESSURE FLASH CHROMATOGRAPHY

(75) Inventors: Lalit Chordia, Pittsburgh, PA (US); Harbaksh Sidhu, Allison Park, PA (US); Todd Palcic, Pittsburgh, PA (US); John Whelan, Mt. Lebanon, PA (US)

(73) Assignee: Waters Technologies Corporation, Milford, MA (US)

( * ) Notice: Subject to any disclaimer, the term of this patent is extended or adjusted under 35 U.S.C. 154(b) by 0 days.

(21) Appl. No.: 13/014,204

(22) Filed: Jan. 26, 2011

(65) Prior Publication Data

US 2011/0180481 A1 Jul. 28, 2011

Related U.S. Application Data

(62) Division of application No. 11/899,059, filed on Sep. 4, 2007, now abandoned.

(60) Provisional application No. 60/841,823, filed on Sep. 1, 2006.

(51) Int. Cl.
*B01D 15/08* (2006.01)

(52) U.S. Cl. ...................................... 210/656; 210/198.2

(58) Field of Classification Search .................. 210/635, 210/638, 656, 659, 137, 143, 198.2
See application file for complete search history.

(56) References Cited

U.S. PATENT DOCUMENTS

| | | | |
|---|---|---|---|
| 4,283,280 A | 8/1981 | Brownlee | |
| 4,293,422 A | 10/1981 | Still | |
| 4,478,720 A | 10/1984 | Perrut | |
| 4,769,141 A | 9/1988 | Couillard | |
| 4,880,543 A | 11/1989 | Khosah et al. | |
| 5,013,443 A | 5/1991 | Higashidate et al. | |
| 5,169,521 A | 12/1992 | Oka et al. | |
| 5,169,522 A | 12/1992 | Shalon et al. | |
| 5,190,658 A | 3/1993 | Vilenchik et al. | |
| 5,190,882 A | 3/1993 | Schulz et al. | |
| 5,238,557 A | 8/1993 | Schneider et al. | |
| 5,322,626 A | 6/1994 | Frank et al. | |
| 5,468,452 A | 11/1995 | Hagiwara | |
| 5,472,612 A | 12/1995 | Maxwell | |
| 5,474,677 A | 12/1995 | Naka | |

(Continued)

FOREIGN PATENT DOCUMENTS

JP 06-170111 A 6/1994

(Continued)

OTHER PUBLICATIONS

Snyder (Introduction to Modern Liquid Chromatography, John Wiley&Sons, New York, 1979, pp. 624-626).*

(Continued)

*Primary Examiner* — Ernest G Therkorn
(74) *Attorney, Agent, or Firm* — McCarter & English, LLP

(57) ABSTRACT

A method for separating a sample using high pressure flash chromatography is provided. The method comprises the steps of: i) providing a pressurized vessel containing an adsorption material; ii) pressurizing a compressible fluid, optionally containing a cosolvent, to create a mobile phase; iii) premixing the sample with the mobile phase or optionally placing the sample in the pressurized vessel; iv) eluting the mobile phase through the pressurized vessel, to obtain a separated sample; v) heating the mobile phase containing the separated sample after the mobile phase exits the pressurized vessel to remove the compressible fluid; and iv) collecting the separated sample. The pressurized vessel contains an adsorption material having a particle size of 10-100 microns, and the pressure of the adsorption vessel is held at 50-350 bar during elution. Also provided is an apparatus for carrying out the above method.

24 Claims, 10 Drawing Sheets

U.S. PATENT DOCUMENTS

| | | |
|---|---|---|
| 5,601,708 A | 2/1997 | Leavesley |
| 5,630,943 A | 5/1997 | Grill |
| 6,063,284 A | 5/2000 | Grill |
| 6,294,088 B1 | 9/2001 | Allington et al. |
| 2002/0185442 A1 | 12/2002 | Maiefski et al. |
| 2003/0173279 A1 | 9/2003 | Aste |
| 2003/0200795 A1 | 10/2003 | Gerner et al. |
| 2004/0262222 A1 | 12/2004 | Chordia et al. |
| 2005/0011835 A1 | 1/2005 | Henderson et al. |
| 2006/0027490 A1 | 2/2006 | DeMarco |
| 2006/0054543 A1 | 3/2006 | Petro et al. |
| 2010/0038299 A1 | 2/2010 | Matabe |

FOREIGN PATENT DOCUMENTS

| | | |
|---|---|---|
| JP | 2003-247988 | 9/2003 |
| JP | 2006-064566 A | 3/2006 |
| JP | 2007-120972 A | 5/2007 |
| WO | 2005066623 | 7/2005 |

OTHER PUBLICATIONS

Snyder (Introduction to Modern Liquid Chromatography, John Wiley&Sons, New York, 1979, pp. 173-183).*

PCT Written Opinion for International application No. PCT/US07/19275, dated Dec. 28, 2007.

PCT Search Report for International application No. PCT/US07/19275, dated Dec. 28, 2007.

European Search Report for EP Application No. 07837675.3, dated Aug. 24, 2011.

* cited by examiner

ACETAMINOPHEN

BENZOIC ACID

ACETAMINOPHEN

BENZOIC ACID

ACETAMINOPHEN

BENZOIC ACID

KETOPROFEN

HIGH PRESSURE FLASH CHROMATOGRAPHY

CROSS-REFERENCE TO RELATED APPLICATION

This application is a divisional application of application Ser. No. 11/899,059, filed Sep. 4, 2007, now abandoned, which claims priority to U.S. Provisional patent application Ser. No. 60/841,823, filed Sep. 1, 2006, the teachings of which are incorporated herein by reference.

BACKGROUND OF THE INVENTION

Chromatography is a technique used to, among other things, separate component elements of a starting material. Within the general field of chromatography, there are several types. Supercritical fluid chromatography (SFC) is a high pressure, reverse-phase method that typically operates above the critical point of the mobile phase fluid, and offers significant speed advantage and resolution over traditional techniques such as high performance liquid chromatography (HPLC). SFC employs carbon dioxide or another compressible fluid as a mobile phase, sometimes with a co-solvent, to perform a chromatographic separation. SFC has a wide range of applicability and typically uses small particle sizes of 3-20 microns for column packing material and is for analytical to preparative scale applications because of the lower pressure drop. In HPLC applications pressure at the top of the column typically reaches up to 1000 psi but pressure at the bottom is reduced to ambient pressure, creating a significant pressure drop.

Liquid chromatography (LC) applies to a cruder, lower pressure, lower performance technique for simple separations. Flash chromatography is a form of adsorptive chromatography and is subset of LC that uses a very simple, porous stationary phase with particle sizes nearer to 100 microns often in a disposable cartridge, or column. Because the particles in the packing material are larger and often irregular, the columns are much cheaper and are considered disposable. Pressure at the top of the column in flash chromato-graphy applications is typically up to 100 psi and dropping down to ambient at the bottom of the column. Still (U.S. Pat. No. 4,293,422) describes a method of adsorptive chromatography in which the mobile phase is first admitted into a space above an adsorbent bed of silica gel, then pushed through the bed with gas pressure. Once the space is cleared, the mobile phase with dissolved compounds for analysis is admitted, and it too is pushed into the bed, displacing the earlier charge of neat mobile phase. Then in a third step, a second charge of neat mobile phase forces the solution through the bed, causing fractionation of the solute. A subsequent disclosure by Andrews (U.S. Pat. No. 4,591,442) describes a similar device, the main difference being in the placement of the liquid holding space. Both disclosures focus on mechanical design and methods for achieving flash chromatography at relatively low pressure. More recently, Ritacco (US App. 2003/0102266) describes a convenient polymer-encased cartridge for use as a single ended flash chromatography column. Anzar (WO/2004-051257, US App. 2005/0287062) describes another type of pre-filled cartridge for flash chromatography. Common features of all of these disclosures are (1) an emphasis on instrumental convenience, and (2) the use of an adsorptive bed that allows for fast, although imprecise, separation of solutes. The disclosures also emphasize gas and liquid chromatography applications of low to moderate pressure.

The majority of all separations in flash chromatography use a normal phase technique with solvents such as methanol, ethanol, hexane, and heptane and occasionally the reverse phase technique with water and acetonitrile. Chemists buy thousands of flash chromatography systems per year to use primarily as a simple, repeatable normal phase purification technique. Because of the vast number of flash chromatography systems in medicinal chemistry laboratories in pharmaceutical research environments, users, insurers, regulators and environmentalists are growing increasingly concerned with the vast amount of toxic waste solvent generated at these sites. Given the obvious problems associated with unsafe, toxic, flammable solvents, a new simple, normal phase technique must be found that is fast and uses less toxic solvents.

SUMMARY OF THE INVENTION

The present invention overcomes problems with issues with flash chromatography by using a compressible fluid. In some embodiments the compressible fluid may be recycled or vented, which eliminates or reduces the cost of recycling waste solvent. Carbon dioxide is a preferred compressible fluid because it is a non-toxic, non-flammable, inexpensive, inert, non-toxic sustainable and renewable resource.

Accordingly, in one aspect the present invention provides a method for separating a sample using high pressure flash chromatography, the method comprising the steps of:
  i) providing a pressurized vessel containing an adsorption material;
  ii) pressurizing a compressible fluid, optionally containing a cosolvent, to create a mobile phase;
  iii) eluting the mobile phase and the sample through the pressurized vessel, to obtain a separated sample;
  iv) heating the mobile phase containing the separated sample after the mobile phase exits the pressurized vessel to facilitate the separation of the compressible fluid; and
  v) collecting the separated sample, wherein the pressurized vessel contains an adsorption material having a particle size of 10-100 microns, and the pressure of the adsorption vessel is held at 50-350 bar during elution.

In another aspect, the present invention provides a high pressure flash chromatography apparatus comprising:
  a) a pressurized vessel containing an adsorption material having a particle size of 10-100 microns;
  b) a pumping means for pressurizing and delivering a mobile phase to the pressurized vessel, the mobile phase comprising a compressible fluid;
  c) a loading means for loading a sample into the pressurized vessel and onto the adsorption material;
  d) a pressure controlling means for controlling the pressure of the mobile phase exiting the pressurized vessel;
  e) a heat exchanger for controlling the temperature of the mobile phase exiting said pressure controlling means;
  f) a collection means for collecting fractions of the sample; and
  g) a means for directing the mobile phase exiting the heat exchanger to the collection means.

These and other aspects of the invention will become more readily apparent from the following drawings, detailed description and appended claims.

BRIEF DESCRIPTION OF THE DRAWINGS

For the present invention to be easily understood and readily practiced, the invention will now be described, for the purposes of illustration and not limitation, in conjunction with the following figures, wherein.

DETAILED DESCRIPTION OF THE INVENTION

Figure 1:
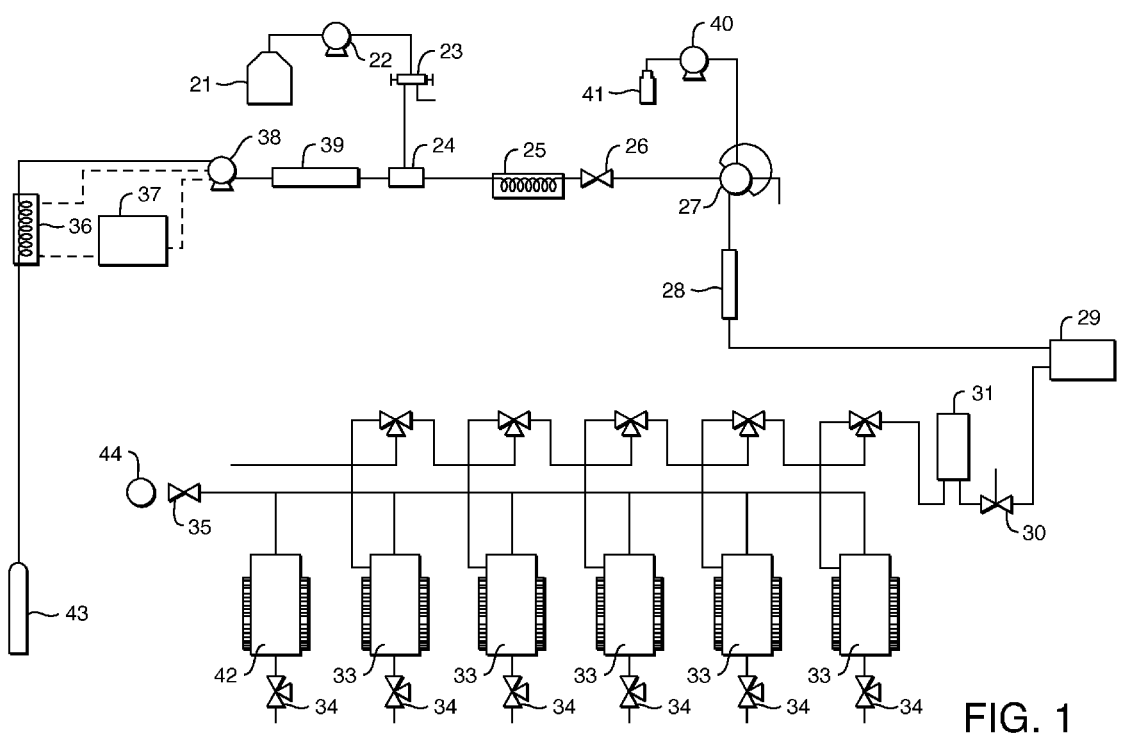
FIG. 1 is a schematic representation of a preferred embodiment of the apparatus of the present invention.

As used herein in the specification and claims, including as used in the examples and unless otherwise expressly specified, all numbers may be read as if prefaced by the word "about", even if the term does not expressly appear. Also, any numerical range recited herein is intended to include all subranges subsumed therein.

A compressible fluid is used as a mobile phase, to elute the sample containing a compound(s) of interest. More than one compressible fluid can be used, e.g., a mixture. Suitable compressible fluids include, for example, carbon dioxide, water, ammonia, nitrogen, nitrous oxide, methane, ethane, ethylene, propane, butane, n-pentane, benzene, methanol, ethanol, isopropanol, isobutanol, monofluoromethane, trifluoromethane, dimethyl sulfoxide, acetonitrile, hydrofluorocarbons, chlorotrifluoromethane, monofluoromethane, hexafluoroethane, 1,1-difluoroethylene, 1,2-difluoroethylene, toluene, pyridine, cyclohexane, m-cresol, decalin, cyclohexanol, O-xylene, tetralin, aniline, acetylene, chlorotrifluorosilane, xenon, sulfur hexafluoride, propane or a combination thereof.

A preferred compressible fluid is carbon dioxide, because it is nontoxic, inexpensive and widely available, as long as the sample requiring separation has some solubility in carbon dioxide.

The mobile phase may also contain a cosolvent, such as an organic solvent. A suitable solvent is chosen based on the polarity of the materials being separated and to increase the solubility of the sample in the compressible fluid. Preferably, the amount of cosolvent is less than 50 wt. %, based on the weight of the compressible fluid and cosolvent mixture combined, more preferably less than 40%, less than 30%, less than 20%, or even less than 10%. It is possible that no cosolvent will be required, although typically at least a small amount is necessary, e.g., about 1-10%, to improve solubility of the sample in the compressible fluid. One skilled in the art can easily select a suitable solvent based on the characteristics of the sample.

The mobile phase may be comprised of a single mobile phase, or more than one mobile phase, e.g., two or more mobile phases, such as three or four. The composition of the mobile phase or phases is determined by the required solvent strength of the mobile phase. Typically, the more polar the solvent mixture, the more polar the compounds that are separated, as would be understood by one skilled in the art. The compressible fluid and cosolvent can be delivered to the pressurized vessel in a mixed stream or in separate streams, according to the needs of the user.

In one embodiment a first mobile phase may be a weaker solvent to elute non-polar entities, while a second or additional mobile phase may be up to 100% of a stronger solvent to increase the solvent strength of the mobile phase and elute polar materials.

The mobile phase or phases may also include gradients. In a preferred embodiment a gradient of the cosolvent is added to the compressible fluid, e.g, the composition of the mobile phase changes over time, over the course of the separation. A gradient, instead of a fixed amount of solvent, may produce quicker or better chromatographic separation because gradients may change the chemical characteristics of the combined stream that elute different compounds under different conditions.

The mobile phase is passed through a pressurized vessel containing an adsorption material, the vessel being pressurized to maintain the compressible fluid at the appropriate pressure. In one embodiment, the sample is first loaded into the pressurized vessel before the mobile phase is added, for example, if the sample is very viscous. In another embodiment, the sample can be premixed with the mobile phase, and the mixture is then loaded in the pressurized vessel. In yet another embodiment, the sample is dissolved in a solvent and introduced into the stream of the cosolvent prior to mixing the compressible fluid with the cosolvent. The solvent can be the same as or different from the cosolvent used in the mobile phase. In another embodiment the sample is injected into the mobile phase.

The present invention in various modes of operation results in rapid equilibration which means that there is very little time required between runs and the next injection can be almost immediately. Unfortunately, in normal phase HPLC, there is significant time spent equilibrating the column before the next run is started.

Suitable chromatography adsorption materials include silica-based materials, such as silica, silica gel or alumina of regular or irregular shape, and other column packing materials known to those skilled in the art of chromatography. A preferred packing material is silica.

Typical packing material in standard flash chromatography includes highly porous, irregular particles of sizes greater than 50 microns. Smaller particles can be used in the present invention than in traditional LC, HPLC or flash chromatography because there is a lower pressure drop from the top of the column to the bottom of the column, resulting from a less viscous mobile phase with higher diffusivities. Preferably, the particle size of the adsorption material used in the present invention is between about 10-100 microns, more preferably between about 20-70 microns.

The pressurized vessel is a cylindrically shaped column made from a material that is capable of withstanding high pressures, such as stainless steel. The vessel can have either or both a top and bottom cap and may be of single piece or multi-piece construction. In one embodiment the adsorption material is dry packed directly into the pressurized vessel. In another embodiment the adsorption material is piston packed using dynamic axial compression (DAC), which provides the capability of rapid packing and unpacking of the adsorption material. In another embodiment a separate cartridge or column containing the adsorption material, which may be prepacked, is inserted into the pressurized vessel. The sample is then loaded into or onto the cartridge and the pressurized vessel is used as support, including pressure reinforcement, for the cartridge. The cartridge may be of a disposable nature and made from any material common to flash chromatography columns, including but not limited to all types of plastic or other non-swelling materials. Furthermore, the cartridge may contain column regeneration features. One or more frits may also be included in the pressure vessel or cartridge. The diameter of the cartridge may be of any size, but preferably between about 1 cm to 20 cm, more preferably between about 2 to 10 cm.

While the mobile phase passes through the pressurized vessel (or flash cartridge within the vessel) containing the adsorption material, back pressure is maintained using a manual or automated back pressure regulator.

A detector is used to detect and separate concentrations of the compound(s) of interest in the sample. Suitable detection devices include, for example, Mass spectroscopy Detector, UV/VIS detector, Evaporative Light Scattering Detector, Flame Ionization detector, Fourier Transform Infrared Spectroscopy Detector, Infrared Detector, or other similar devices known to one skilled in the art. The detector can be placed either before or after the back pressure regulator. The nature of the detection does not limit the practice of the present invention.

After the mobile phase passes through the pressurized vessel or flash cartridge and the back pressure regulator, it passes through a heater. The heat from the heater makes sure that part of the mobile phase that is not a liquid solvent is converted into a gas. After the mobile phase passes through the heater, the desired and undesired fractions of the sample are collected. Any standard collection method/apparatus used in chromatographic separations can be used. Suitable collection means include, but are not limited to, fraction collectors and cyclonic separators. Also suitable are trapping devices such as a solid phase cartridge or a cryofocusing system. Undesired fractions are directed to waste collectors.

After the separation and prior to the transfer of the mobile phase to collection, additional compressible fluid and/or solvent can be added to the mobile phase. This typically occurs after the mobile phase exits the back pressure regulator, and can be a manual or automated addition, and is used to reduce the aerosolizing effect on the separated sample. If the stream exiting the back pressure regulator aerosolizes, the separated sample may drop out and clog the lines to the collection means. In certain applications, by adding additional fluid the amount of the separated sample that is recovered is increased. The solvent can be the same as or different from the original cosolvent used in the mobile phase.

Also after the separation and prior to transfer to the collection system, the mobile phase is heated to vaporize the compressible fluid.

Operating parameters such as pressure and temperature depend on the specific physical and chemical characteristics of the compound of interest in the sample, and can be determined by one skilled in the art. In a preferred embodiment of the present invention, the mobile phase is maintained at a pressure of between about 50 bar to 350 bar. More preferably, the pressure of the mobile phase is maintained at a pressure of between about 70 to 150 bar at the top of the pressurized vessel or flash cartridge. The pressure change across the pressurized vessel or flash cartridge from the top to the bottom is preferably between about 1-100 bar and more preferably between about 1-20 bar. Most preferably the pressure change is between about 5-10 bar. Since the pressure of the mobile phase is higher than in traditional LC or HPLC techniques, the mobile phase is less viscous and has higher diffusivities. A less viscous mobile phase translates into a reduced pressure drop across the column or cartridge. A mobile phase with higher diffusivities provides faster separations. By using a compressible fluid such as carbon dioxide as the mobile phase the present invention reduces or eliminates the use of organic solvents used in flash chromatography. Additionally, the mobile phase can be used by itself to accomplish pressure equalization between the inside and the outside of the cartridge, when a cartridge is used.

The temperature of the pressurized vessel is typically held at between about 10° C. to 150° C., more preferably ambient temperature to about 80° C., the temperature selection being based on the type of sample, the particle size of adsorption material and other operating parameters.

There is no pure limitation on the flow rate of the mobile phase. Rather the flow rate is limited by the pressure change across the pressurized vessel or flash cartridge, which is a function of the particle size of the adsorption material and the flow rate. The method of the present invention is much faster than conventional flash separation, taking between about 30 to 70% less time than conventional flash methods. The flow rate is typically related to the size of the column. For the same size column, the delta pressure (change in pressure from the top of the column to the bottom of the column) generated is an order of magnitude lower as compared to running pure incompressible solvents. This means for the same flow rate, the method of the present invention will be about 4 to 10 times faster from the time of injection to the time of collection than conventional flash chromatography, when all other parameters such as flow rate, size of column, packing of adsorption material in the column and particle size of the adsorption material are otherwise the same.

FIG. 1 illustrates an embodiment of the present invention. The compressed fluid supply 43 is opened to allow the compressed fluid to flow through a pre cooling heat exchanger 36 which is controlled by a water bath 37. The compressed fluid reaches the compressible fluid pump 38 and is pumped through a dampener 39 and into a mixing chamber 24. Types of compressible fluid pumps include but are not limited to, reciprocating and syringe pumps. Any pump of the present invention may also be a compressor. The cosolvent supply 21 is first primed to remove bubbles through the cosolvent pump 22 using a prime valve 23. After priming the cosolvent, pump 22 is activated and the cosolvent is pumped into the mixing chamber 24 where the cosolvent and compressible fluid are mixed to create the mobile phase. The mobile phase goes through a second heat exchanger 25 where it reaches its desired operating temperature, which, as described above, depends on various other operating parameters and the nature of the sample. A suitable operating temperature can be determined by one skilled in the art. Isolation valve 26 is used when changing the pressurized vessel 28, cartridges in the pressurized vessel 28 or when samples are loaded directly into the pressurized vessel 28.

Figure 3:
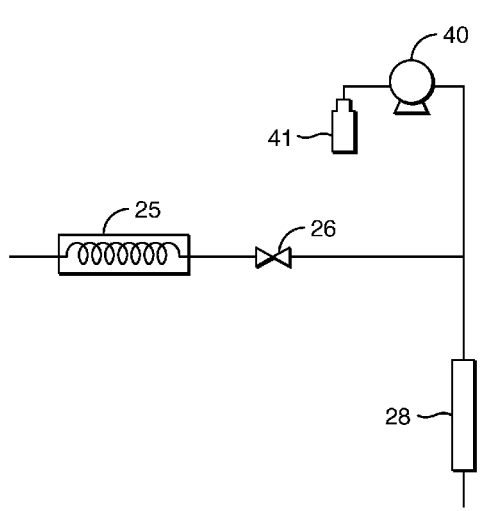
FIG. 3 is a schematic representation of an alternative embodiment for loading sample into the pressurized vessel.
Figure 4:
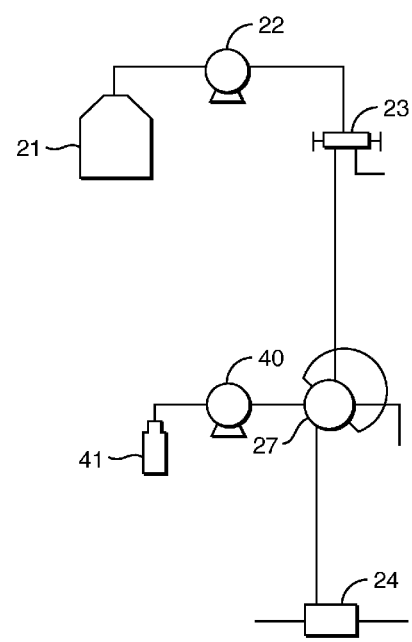
FIG. 4 is a schematic representation of another alternative embodiment for loading sample into the pressurized vessel.

Sample introduction into the pressurized vessel 28 is achieved one of several ways. In an embodiment shown in FIG. 1, the sample solution 41 is introduced into the mobile phase by first pumping it with the injection pump 40 into a sample loop, and then the sample loop is brought into the mobile phase by the injection valve 27. In another embodiment shown in FIG. 3, the sample is introduced using a sample reservoir 41 with only an injection pump 40 and no injection valve. The sample in the mobile phase enters the pressurized vessel 28 and continues on to the detector 29. In both of these embodiments, the sample is introduced between the isolation valve 26 and the pressurized vessel 28. In another embodiment shown in FIG. 4, the sample is introduced between the prime valve 23 and the mixing chamber 24.

After passing through the detector the mobile phase with the sample exits a third valve 30 and the compressed fluid is vaporized in the heat exchanger 31. Collection of the desired separated sample(s) can either be done automatically through software settings or manually. Collection valves 32 are activated at certain times and the desired separated sample(s) continue into the sample collectors 33 and then into collection containers 34. When there is no desired separated sample in the mixed mobile phase the mixed mobile phase goes to a waste collector 42 and then into the collection containers 34. To keep nominal pressure on the sample collectors 33 a back pressure valve 35 is used and then the exhaust gas goes to a vent 44. The back pressure valve 35 may be manual or automated, and the exhaust gas may be recycled back to a pre-cooling heat exchanger 36 instead of being vented. Recycling can be achieved by maintaining a higher collection pressure and in one instance includes the following components in a recycling system: 1) cooling water bath 2) condenser, 3) and storage tank.

Figure 2:
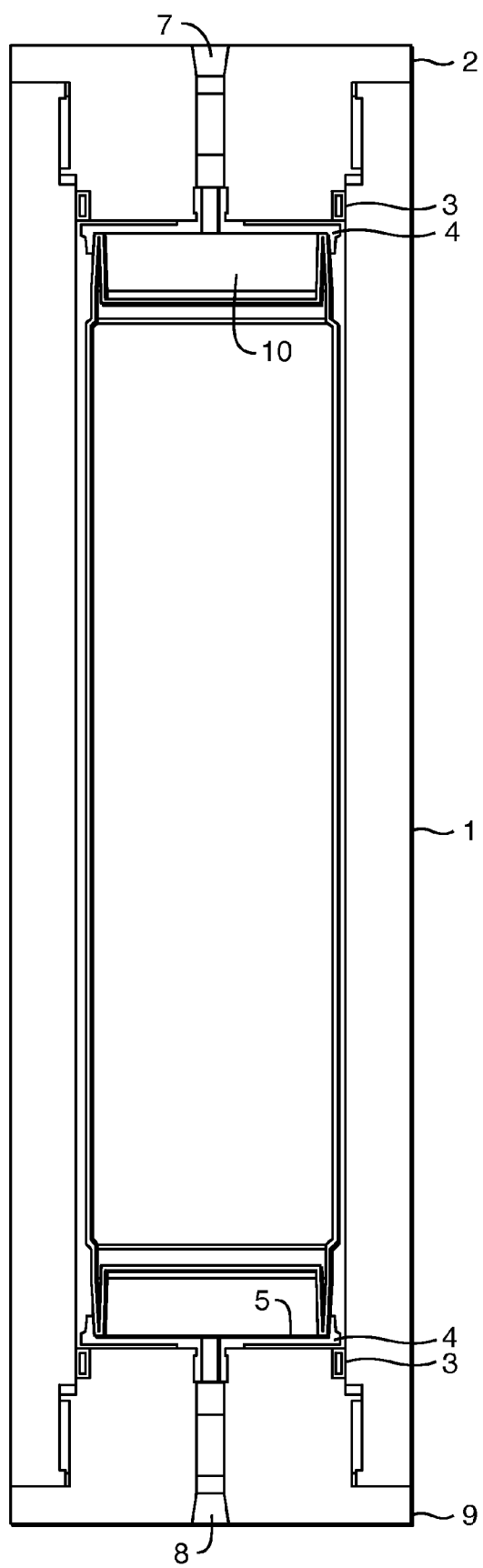
FIG. 2 is a schematic representation of a preferred embodiment of the pressurized vessel of the present invention.

FIG. 2 is an enlargement of the pressurized vessel 28 shown in FIG. 1, and illustrates a preferred embodiment of the pressurized vessel 28, a vessel assembly 1. A separate flash cartridge 6 is inserted into the vessel assembly 1, which has a top cap (2) and a bottom cap 9. There is one seal 3 for each of top cap 2 and bottom cap 9 to seal it with the vessel assembly 1. The top and the bottom of the cartridge 6 is held in place by two holders 4 that are connected (separately) to the top cap 2 and to the bottom cap 9. There is another seal 5 to seal the cartridge to the holder. The mobile phase enters the vessel assembly 1 through port 7 and exits from port 8. Optionally, there is a sample loading cavity at the top of the flash cartridge 10. In another preferred embodiment the adsorption material is dry packed directly into the vessel assembly 1 instead of using the separate flash cartridge 6 filled with adsorption material.

EXAMPLES

For the purposes of the examples below, the following experimental set up was used. The flash cartridge packed with silica (Biotage with 60A Kp-Silica, 43-60 microns, and a 75.times.300 mm bed) was placed in the pressurized vessel (Thar 5 L vessel) and the cap 2 to the vessel assembly is closed. The sample to be separated was dissolved in a suitable cosolvent. The compressible fluid pump 38 (Thar P-200) and the cosolvent pump (Thar P-50) were started and allowed to reach the desired flow rates. The pressure was maintained by a valve 30 to the desired pressure. The mobile phase passed through a detector (Gilson UV detector) and onto a valve (Thar ABPR 200) that controls the back pressure on the flash cartridge. While passing through the detector, a signal is relayed to the collection valves as to when to start collection into the desired fractions. The mobile phase with the separated sample passed through another heat exchanger that vaporized the compressible fluid into a gaseous state to allow the liquid to be more easily collected as fractions. The fractions were collected in a collection means (Thar CS-1L). All analysis of the fractions was conducted on a Thar SFC Method Station using an AD-H column from Chiral Technologies. The fractions were dissolved to create a 10 mL solution. The flow rate of the compressible fluid (carbon dioxide) was 3.4 mL/min and 0.6 mL/min of co-solvent (methanol). The amount of co-solvent was held constant at 15%. Back pressure was maintained at 100 bar. A photo diode array detector from Waters Corporation was used as the detection means with a signal frequency of 245 nanometers to 300 nanometers. Temperature was maintained at 40° C.

Example 1

Figure 5:
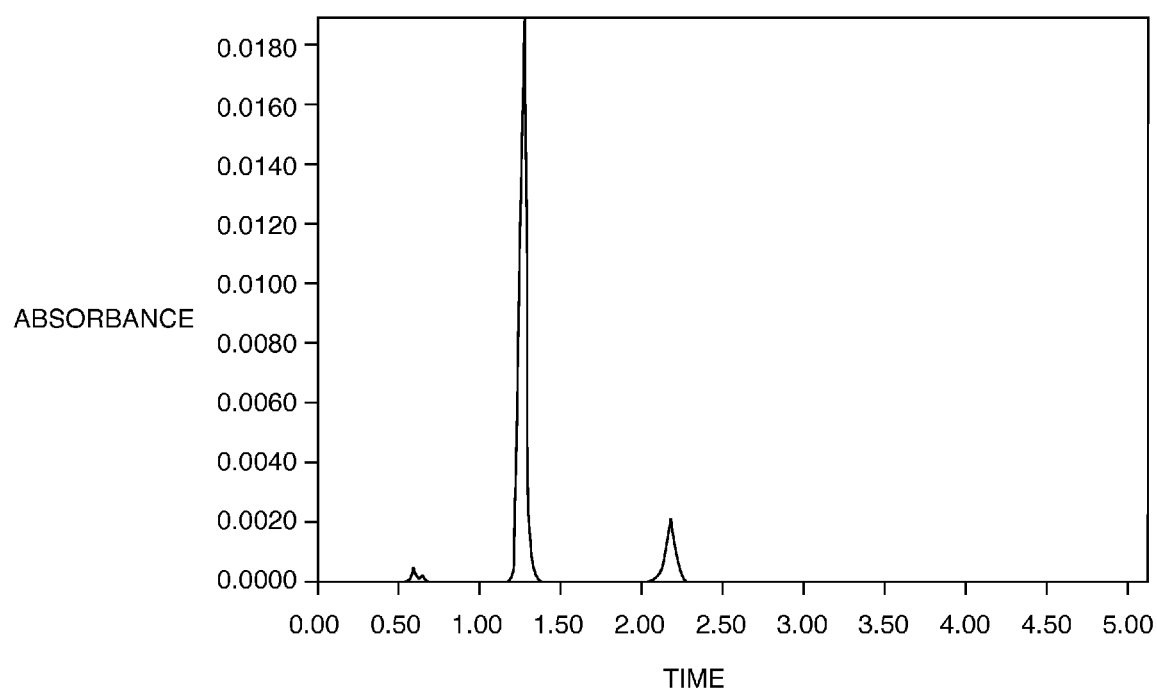
FIGS. 5 and 6 are chromatograms showing the separation in Example 1.
Figure 6:
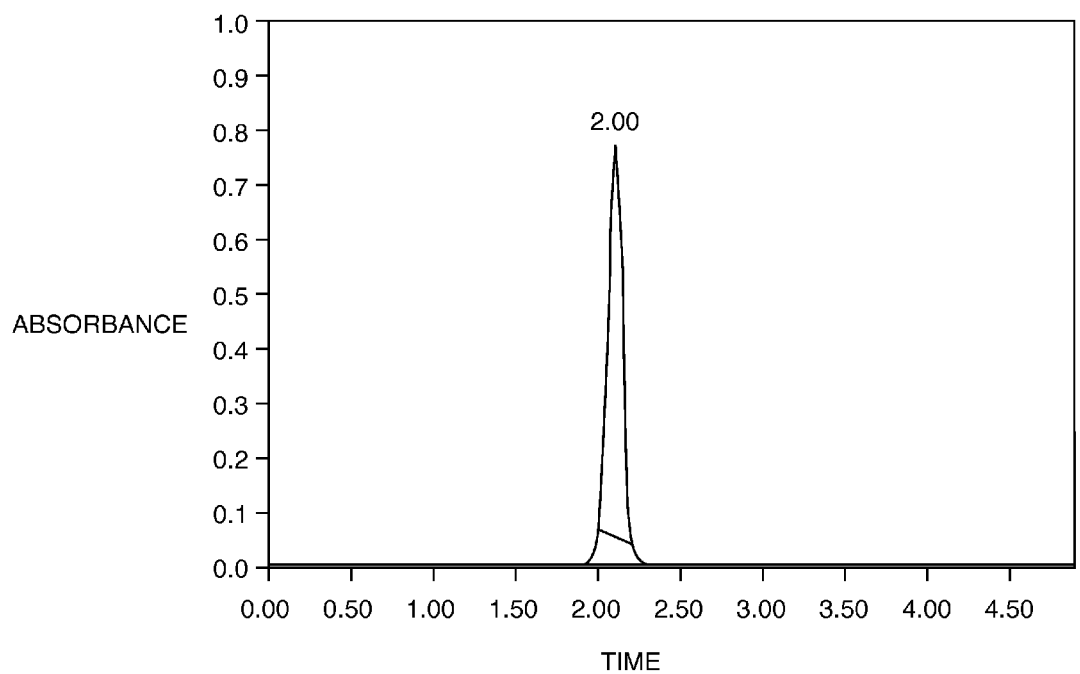

6.5 g of an Acetaminophen-Benzoic Acid sample solution was dissolved in 100 ml of methanol at standard temperature and pressure (STP). The total flow rate was set at 150 g/min with the main compressed fluid being carbon dioxide, with a gradient of 5%-35% methanol over 10 minutes and thereafter it was maintained at 35%. The operating conditions were as follows: 1) back pressure on the flash cartridge was maintained at 100 bar 2) temperature of the mobile phase (carbon dioxide and methanol) was maintained at 35 C; and 3) the heat exchanger was maintained at 35 C. Technically the pressure in the vessel is the back pressure on the cartridge+the delta pressure across the cartridge. Since the delta P is small, the pressure in vessel is nearly the same as the back pressure. The sample was introduced into the system using an injector loop and 230 mg of the sample was loaded. Two fractions from these injections were collected. Using the Thar Superchrom software fraction 1 was found to be 98% pure of Acetaminophen, and fraction 2 to be 99.9% pure of Benzoic Acid. FIGS. 5 and 6 illustrate the separation.

Example 2

Figure 7:
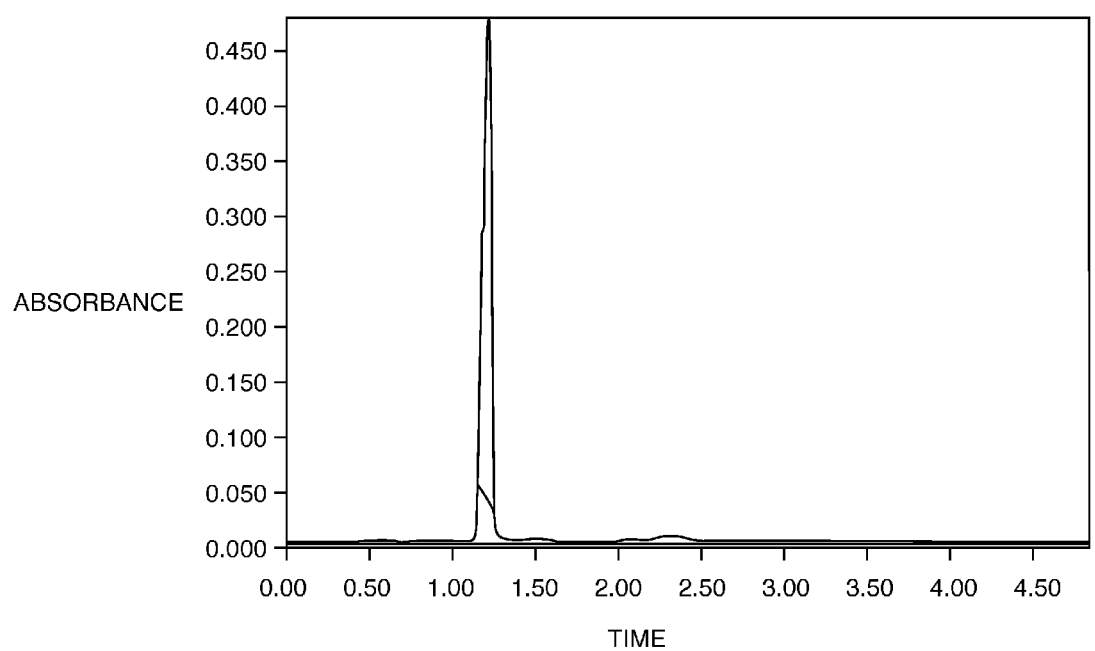
FIGS. 7 and 8 are chromatograms showing the separation in Example 2.
Figure 8:
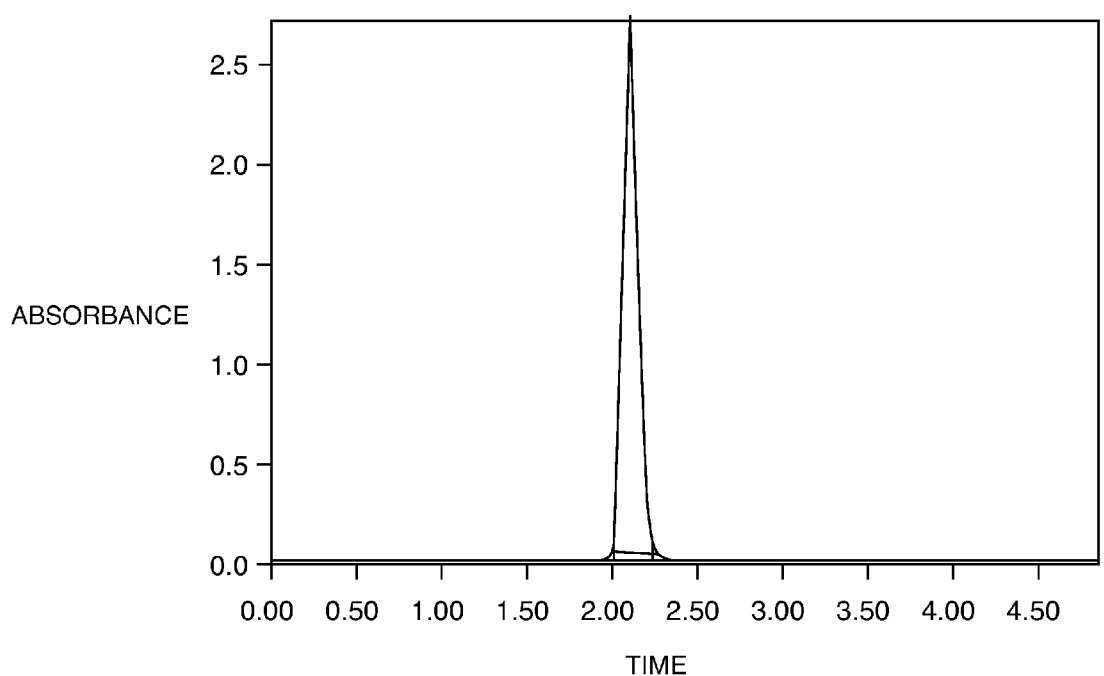

3.5 g of a sample containing 1.3052 g of Acetaminophen and 2.1947 g of Benzoic Acid was dissolved in 50 ml of methanol at STP and loaded directly onto a sample loading cavity at the top of the flash cartridge. The pressurized vessel was then closed and carbon dioxide, as the mobile phase, was introduced into the system and allowed to equilibrate. Carbon dioxide was pumped at 150 g/min with a gradient of 5%-35% methanol over 10 minutes, and thereafter it was maintained at 35%. The operating conditions were as follows: 1) back pressure was maintained at 100 bar; 2) temperature of the mixed mobile phase (carbon dioxide and methanol) was maintained at 35° C.; and 3) the heat exchanger was maintained at 35° C. Sample fractions were collected. Using the Thar Superchrom software fraction 1 found to be 99% pure Acetaminophen, and fraction 2 to be 99.9% pure Benzoic Acid. FIGS. 7 and 8 illustrate the separation.

Example 3

Figure 9:
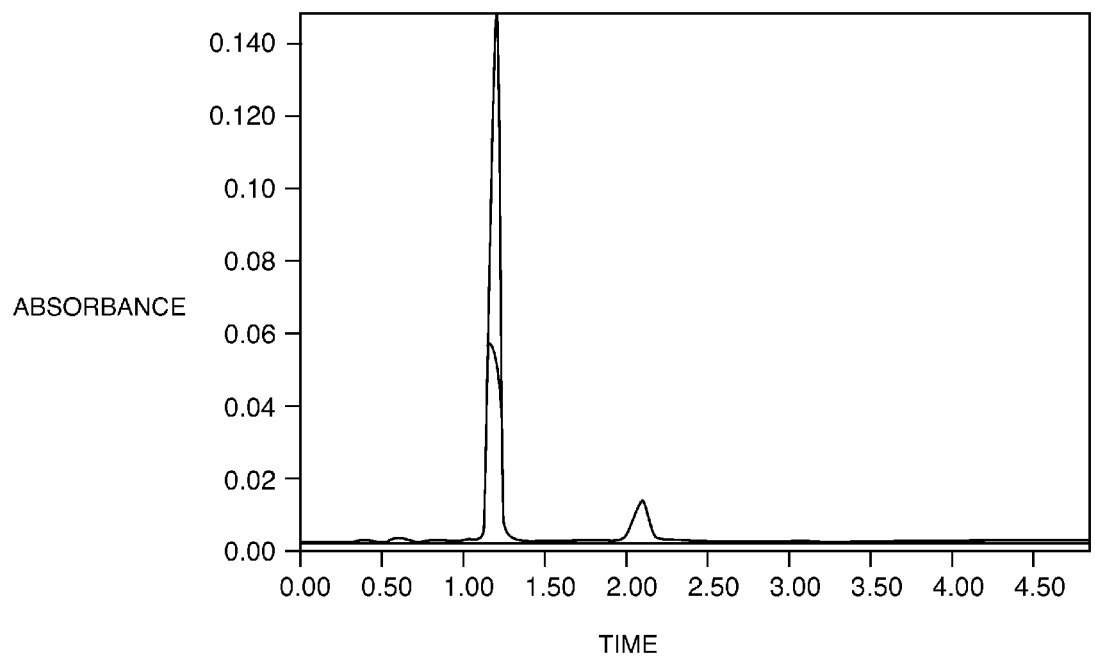
FIGS. 9 and 10 are chromatograms showing the separation in Example 3.
Figure 10:
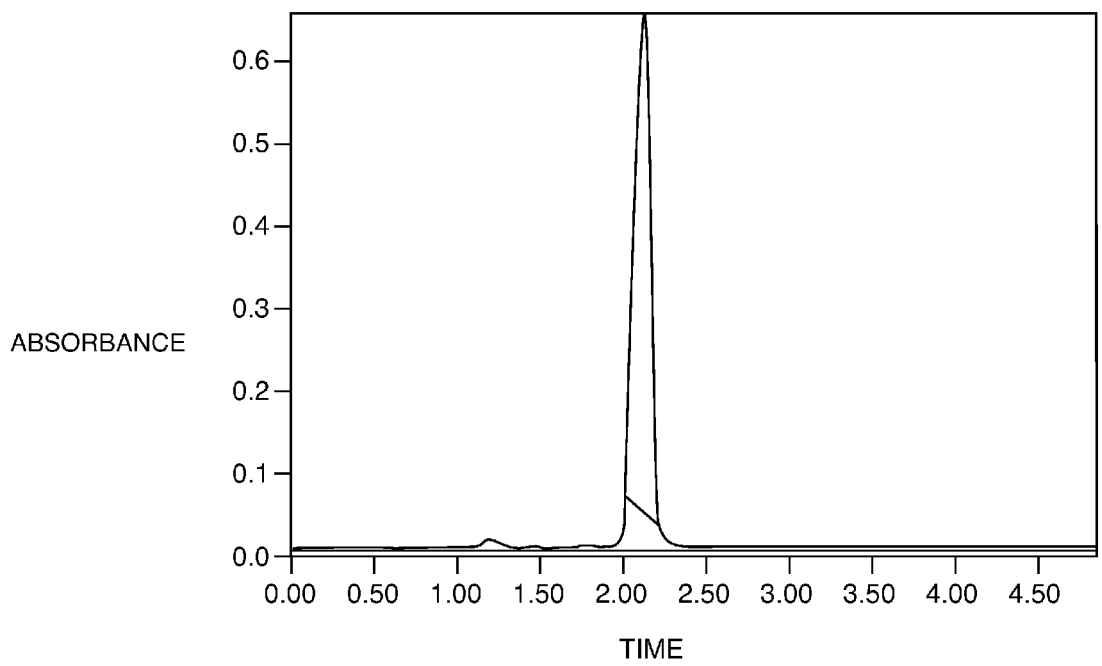

7.18869 g of a sample containing 2.85839 g of Acetaminophen and 4.3303 g of Benzoic Acid was dissolved in methanol at STP. Carbon dioxide was the compressible fluid and was pumped at 150 g/min. A mobile phase was created with a gradient of 5%-35% methanol over 10 minutes, and thereafter it was maintained at 35%. The operating conditions were as follows: 1) back pressure maintained at 100 bar; 2) temperature of the mobile phase (carbon dioxide and methanol) was maintained at 35° C.; and 3) the heat exchanger was maintained at 35° C. The sample was loaded into the mobile phase using an injection pump through a tee immediately before the column. 718 mg of sample was loaded onto the column. Fractions from these injections were collected. Using the Thar Superchrom software fraction 1 was found to be 86% pure Acetaminophen, and fraction 2 to be 99.9% pure Benzoic Acid. FIGS. 9 and 10 illustrate the separation.

Example 4

Figure 11:
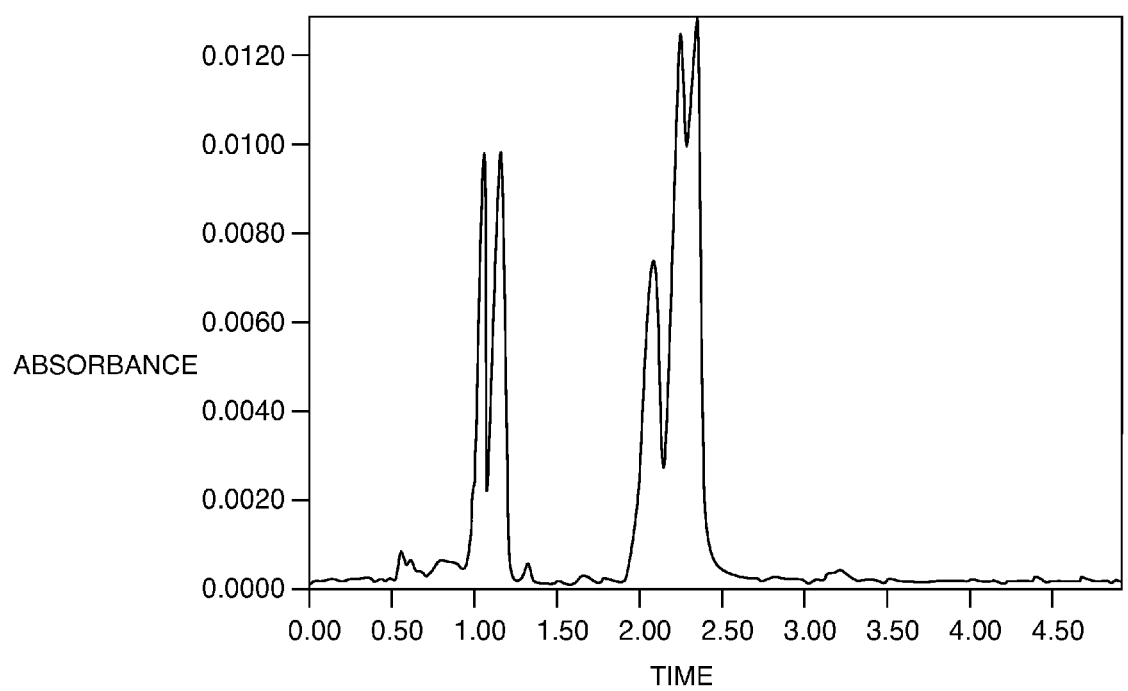
FIG. 11 is a chromatogram showing the separation in Example 4.

2.90041 g of a sample containing 0.32197 g of Ketoprofen was dissolved in methanol at STP. Carbon dioxide was the compressible fluid and was pumped at 150 g/min. A mobile phase was created with a gradient of 5%-35% methanol over 10 minutes, and thereafter it was maintained at 35%. The operating conditions were as follows: 1) back pressure maintained at 100 bar; 2) temperature of the mixed mobile phase (carbon dioxide and methanol) was maintained at 35° C.; and 3) the heat exchanger was maintained at 35° C. The sample was loaded using an injection loop. 101 mg of sample was injected onto the flash cartridge through the injection loop. Fractions from these injections were collected. Using the Thar Superchrom software fraction 1 was found to have increased the concentration of Ketoprofen to 30% pure. FIG. 11 illustrates the purification.

Various elements of the present invention can be practiced individually or in any combination thereof without any limitation. All elements disclosed in the present disclosure can be practiced within the context of various industries including but not limited to, pharmaceuticals, fine chemicals, nutraceuticals, coatings, and petrochemical industries.

The invention claimed is:

1. A method for separating a sample using high pressure flash chromatography, the method comprising the steps of:
   i) providing a pressurized vessel and a cartridge encapsulated therein, wherein the cartridge defines an adsorption material chamber having a diameter between about 1 cm to 20 cm and containing an adsorption material;
   ii) pressurizing a compressible fluid, optionally containing a cosolvent, to create a mobile phase;
   iii) eluting the mobile phase and the sample through the pressurized vessel under high pressure flash chromatography conditions, to obtain a separated sample;
   iv) heating the mobile phase containing the separated sample after the mobile phase exits the pressurized vessel to facilitate the separation of the compressible fluid; and
   v) collecting the separated sample,
   wherein the pressurized vessel contains an adsorption material having a particle size of 10-100 microns, and the pressure of the adsorption vessel is held at 50-350 bar during elution.

2. The method of claim 1, wherein the mobile phase is heated before entering the pressurized vessel.

3. The method of claim 1, wherein the sample is loaded directly onto the cartridge within the pressurized vessel.

4. The method of claim 1, wherein the sample is premixed with the mobile phase prior to elution through the pressurized vessel.

5. The method of claim 1, wherein the mobile phase is recycled after collecting the separated sample.

6. The method of claim 1, wherein the compressible fluid is carbon dioxide.

7. The method of claim 1, wherein the cosolvent is an organic solvent.

8. The method of claim 1, wherein said adsorption material is a silica-based material.

9. The method of claim 1, wherein the mobile phase comprises a compressible fluid and a cosolvent.

10. The method of claim 9, wherein the amount of cosolvent is less than 50 wt % of the mobile phase.

11. The method of claim 9, wherein the amount of cosolvent is less than 40 wt % of the mobile phase.

12. The method of claim 9, wherein the amount of cosolvent is less than 30 wt % of the mobile phase.

13. The method of claim 9, wherein the amount of cosolvent is less than 20 wt % of the mobile phase.

14. The method of claim 9, wherein the amount of cosolvent is less than 10 wt % of the mobile phase.

15. The method of claim 1, wherein the sample is loaded into the cosolvent prior to being mixed with the compressible fluid.

16. The method of claim 1, wherein the cartridge defines an adsorption material chamber having a diameter between about 2 cm to 10 cm.

17. The method of claim 1, wherein the mobile phase is maintained at a pressure of between about 70 to 150 bar at the top of the pressurized vessel or flash cartridge.

18. The method of claim 1, wherein the pressure change across the pressurized vessel or flash cartridge from the top to the bottom is between about 1-100 bar.

19. The method of claim 1, wherein the pressure change across the pressurized vessel or flash cartridge from the top to the bottom is between about 1-20 bar.

20. The method of claim 1, wherein the pressure change across the pressurized vessel or flash cartridge from the top to the bottom is between about 5-10 bar.

21. The method of claim 1, wherein the temperature of the pressurized vessel is held at between about 10° C. to 150° C.

22. The method of claim 1, wherein the temperature of the pressurized vessel is held at between ambient temperature to about 80° C.

23. The method of claim 1, wherein the particle size is between about 20 to about 70 microns.

24. The method of claim 1, wherein the particle size is less than about 50 microns.

* * * * *